(12) United States Patent
Giri et al.

(10) Patent No.: US 8,658,110 B2
(45) Date of Patent: *Feb. 25, 2014

(54) FLUID DELIVERY SYSTEM

(75) Inventors: Manish Giri, Corvallis, OR (US);
Joshua M. Yu, Corvallis, OR (US);
Kevin F. Peters, Corvallis, OR (US);
Paul J. Bruinsma, San Diego, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 1206 days.

This patent is subject to a terminal disclaimer.

(21) Appl. No.: 11/837,749

(22) Filed: Aug. 13, 2007

(65) Prior Publication Data
US 2009/0047440 A1    Feb. 19, 2009

(51) Int. Cl.
*B01L 3/00* (2006.01)

(52) U.S. Cl.
USPC ........... 422/500; 422/501; 422/502; 422/503; 422/504; 422/507; 436/180

(58) Field of Classification Search
USPC ........ 422/99–100, 500–504, 507; 347/44, 47, 347/63, 94; 436/180
See application file for complete search history.

(56) References Cited

U.S. PATENT DOCUMENTS

| | | | |
|---|---|---|---|
| 4,929,238 A | 5/1990 | Baum | |
| 5,178,138 A | 1/1993 | Walstrom et al. | |
| 5,337,738 A | 8/1994 | Heinonen | |
| 5,994,696 A | 11/1999 | Tai et al. | |
| 6,210,359 B1 | 4/2001 | Patel et al. | |
| 6,221,653 B1 | 4/2001 | Caren et al. | |
| 6,323,043 B1 | 11/2001 | Caren et al. | |
| 6,399,396 B1 | 6/2002 | Bass | |
| 6,446,642 B1 | 9/2002 | Caren et al. | |
| 6,458,583 B1 | 10/2002 | Bruhn et al. | |
| 6,461,812 B2 | 10/2002 | Barth et al. | |
| 6,527,368 B1 * | 3/2003 | Giri et al. | 347/44 |
| 6,610,129 B1 | 8/2003 | Sader et al. | |
| 6,746,107 B2 * | 6/2004 | Giere et al. | 347/65 |
| 6,797,469 B2 | 9/2004 | Caren et al. | |
| 6,866,825 B2 | 3/2005 | Chiou et al. | |
| 6,884,580 B2 | 4/2005 | Caren et al. | |
| 6,935,727 B2 | 8/2005 | DaQuino et al. | |
| 7,008,037 B2 | 3/2006 | Caren et al. | |
| 7,026,124 B2 | 4/2006 | Barth et al. | |
| 7,128,398 B2 | 10/2006 | DaQuino et al. | |
| 7,677,695 B2 * | 3/2010 | Giri et al. | 347/44 |
| 2001/0051334 A1 | 12/2001 | Barth et al. | |
| 2002/0094304 A1 | 7/2002 | Yang et al. | |
| 2003/0148539 A1 | 8/2003 | van Dam et al. | |
| 2003/0184611 A1 | 10/2003 | Kuo et al. | |
| 2006/0051250 A1 | 3/2006 | Gonzalez et al. | |
| 2007/0031293 A1 | 2/2007 | Beatty | |

FOREIGN PATENT DOCUMENTS

| | | |
|---|---|---|
| EP | 0280347 | 8/1988 |
| EP | 1 205 247 | 5/2002 |
| EP | 1 245 530 | 10/2002 |
| EP | 1 321 190 | 6/2003 |
| WO | WO 97/44134 | 11/1997 |

OTHER PUBLICATIONS

International Search Report for Application No. PCT/US2008/072131. Report issued Dec. 10, 2008.
EPO, Supplementary EP Search Report for appln. No. EP 08797137.0-2113, dated Jul. 16, 2010.

* cited by examiner

*Primary Examiner* — Jyoti Nagpaul (57) ABSTRACT

Embodiments of a fluid delivery system are disclosed.

12 Claims, 4 Drawing Sheets

FLUID DELIVERY SYSTEM

BACKGROUND

High-throughput research applications often employ automated liquid handling techniques and/or technologies to transfer very small or minute volumes of fluid from one source to another destination. Such transfers generally involve substantially high levels of precision, which may be limited by available technologies. Often, the transfer of precise, minute volumes of a concentrated fluid involves diluting the fluid to a lower concentration and accordingly a larger volume which may be sufficiently more manageable and/or workable within the limitations of existing sample transfer technologies.

BRIEF DESCRIPTION OF THE DRAWINGS

Features and advantages of embodiment(s) of the present disclosure will become apparent by reference to the following detailed description and the drawings, in which like reference numerals correspond to similar, though perhaps not identical components. Reference numerals having a previously described function may or may not be described in connection with other drawings in which they appear.

DETAILED DESCRIPTION

Embodiments of the fluid transfer device disclosed herein are advantageously used to transfer substantially precise and minute volumes of a fluid sample from one source to another destination. Precious fluids that demand high-performance sample transfer methods include, for example, candidate drug compounds in DMSO, aqueous cell lycates, extracted or amplified DNA, blood components, or the like. It is believed that embodiments of the fluid transfer device are configured for single or multiple transfers per use, controlled delivery rates and volumes, and/or reduced waste. Such advantages are attributable, at least in part, to the inclusion of a die (also known as a chip) configured to wick the sample fluid and maintain the sample fluid via capillary forces. The size of the die is advantageously configured to be immersed into a fluid-filled well-plate. The small die includes a fluid slot with small dimensions, which is believed to minimize the load volume (and thus dead volume) and enable substantial capillary pressures to adequately drive the wicking process. It is further believed that the small die size, in combination with the relatively open fluid slot, substantially simplifies the wicking process and the cleaning process, and substantially reduces waste.

The combination of such a die with inkjet dispensing technology enables a predetermined volume of the fluid in the die to be dispensed to a desirable fluid destination in a controlled manner. It is believed that this combination enables such precise and controlled transfer of minute volumes of fluid, without producing undesirable amounts of waste volume. It is further believed that this combination enables wicking and dispensing to be accomplished without using traditional mechanically actuated processes (e.g., pipettes), thereby reducing the potential for fluid contamination.

The fluid dispensing device disclosed herein may also advantageously be cleaned and re-used after a single fluid transfer or after multiple fluid transfers. It may be desirable to clean the device after a single fluid transfer, for example, when it is desirable to transfer a different fluid.

As defined herein, the terms "very small volume" and "minute volume" both refer to a volume ranging from about 1 picoliter (pL) or a fraction thereof to about 10 microliters ($\mu$L) of fluid, and in some embodiments, up to about 50 $\mu$L of fluid. In a non-limiting example, the wicked volume ranges from about 50 nL to several $\mu$L, and the dispensed volume ranges from 1 pL to several $\mu$L. In another non-limiting example, the individual volume of dispensed drops ranges from about 1 pL to about 300 pL.

Generally, the transferred volume may be as small as a single drop ejected from a single nozzle or may include a defined number of drops ejected from one or more nozzles in the fluid transfer device. The fluid transferred may include thousands of drops, to hundreds of thousands of drops, up to millions of drops, and as such, the range of fluid amounts is digital and nearly continuous over at least six orders of magnitude dynamic range. It is to be understood that the maximum volume transferred is limited by the initial wicking volume in the fluid transfer device. It is to be further understood, however, that greater transfer volumes may be achieved by applying multiple fill and dispense cycles.

Individual drop volumes are primarily determined by the dimensions of the fluid ejector device (e.g., an inkjet resistor), ejection chamber size, nozzles, and fluid channels. The drop volume may also be influenced by the energy settings for drop ejection and the fluid properties. For example, the drop weights of ethanol solutions tend to be about 60% of those for aqueous solutions, yet both may be highly reproducible, due, at least in part to the highly reproducible ejection events and further averaging benefits of multiple ejection events.

Operation of the fluid transfer devices disclosed herein may include calibration runs to determine the drop weight for a fluid at fixed energy settings. In an embodiment, the average drop weight may be determined gravimetrically by ejecting a set number of drops into a collection pan and weighing the mass increase in the pan. Drop weight may also be determined by calorimetric methods using a known concentration of a dye in the transfer solution. A set number of drops are ejected into a fluid sample with a known volume of water or other solvent. The dye concentration in the fluid sample or samples is measured optically, for example, by UV-VIS absorption, to determine the dilution factor, and in turn, the average drop weight.

The amount of dye added to the fluid for drop weight calibration is selected in consideration of the solubility of the dye in the solvent, the color intensity of the dye, and any other suitable factors. Typical amounts of dye range from about 0.1 wt % to about 10 wt % of the fluid, and in one embodiment, from about 0.1 wt % to about 5 wt %. Colored dyes may be more desirable than black dyes, although it is to be understood that suitable inkjet ink dye may be employed. Non-limiting examples of suitable dyes include Direct Blue 199 (available from Avecia as Projet Cyan Special), Acid Blue 9; Direct Red 9, Direct Red 227, Magenta 377 (available from Ilford AG, Rue de l'Industrie, CH-1700 Fribourg, Switzerland), Acid Yellow 23, Direct Yellow 132, Direct Yellow 86, Yellow 104 (Ilford AG), Direct Yellow 4 (BASF), Yellow PJY H-3RNA (Avecia), Direct Yellow 50 (Avecia), Direct Blue 199, Magenta 377, or Ilford Yellow 104.

It is to be understood that the term "connect/connected/connecting" is broadly defined herein to encompass a variety of divergent connection arrangements and assembly techniques. These arrangements and techniques include, but are not limited to (1) the direct connection between one component and another component with no intervening components therebetween; and (2) the connection of one component and another component with one or more components therebetween, provided that the one component being "connected to" the other component is somehow operatively connected to the other component (notwithstanding the presence of one or more additional components therebetween).

Figure 1A:
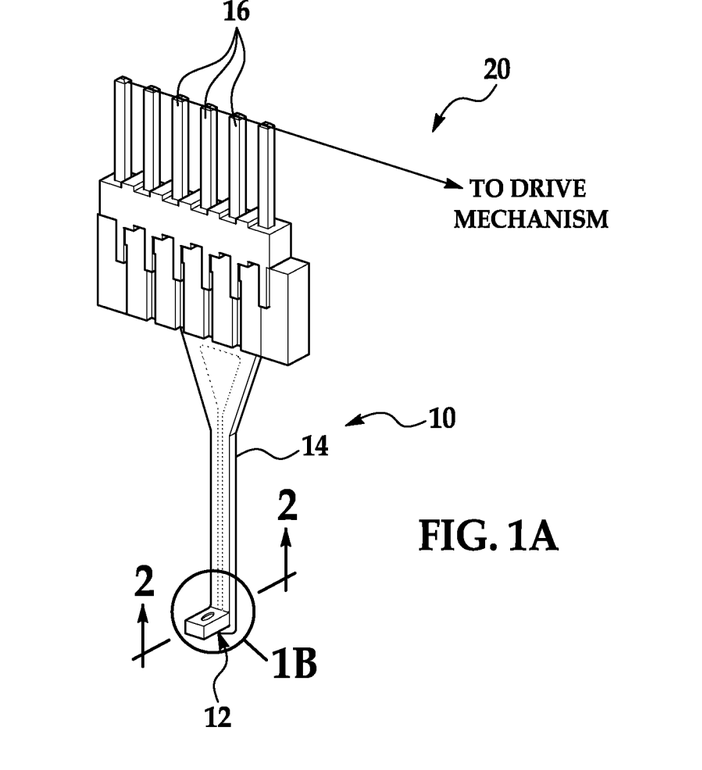
FIG. 1A is a semi-schematic perspective view of an embodiment of a fluid transfer device and a fluid transfer system.
Figure 1B:
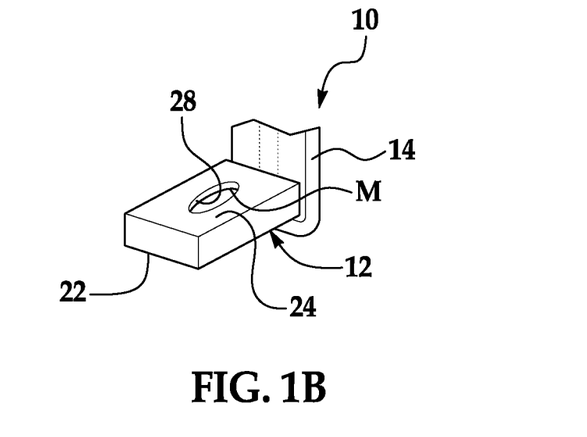
FIG. 1B is an enlarged view of a die of the embodiment of the fluid transfer device shown in FIG. 1A.
Figure 2A:
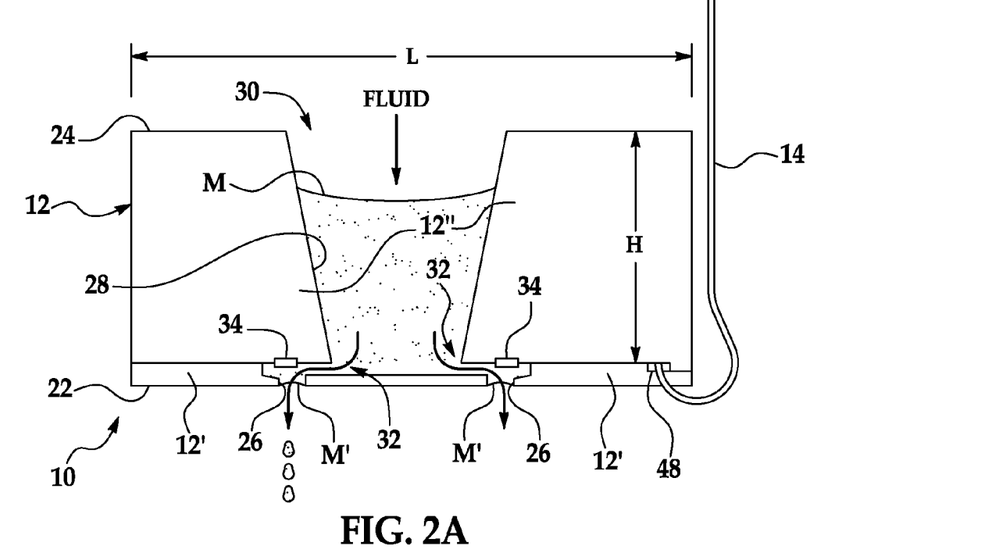
FIG. 2A is a cross-sectional, cut-away view of the embodiment of the fluid transfer device taken along line 2-2 of FIG. 1A, wherein the device is filled with a sample fluid and the black lines indicate sample fluid flow upon ejection.

Referring now to FIGS. 1A, 1B and 2A together, embodiments of a fluid transfer system 20 (FIG. 1A) including the fluid transfer device 10 (FIG. 1A) and the die 12 thereof (FIGS. 1B and 2A) are depicted. Very generally, and as shown more clearly in FIGS. 1B and 2A, the fluid transfer device 10 includes the die 12 having first and second opposed surfaces 22, 24, at least one nozzle 26 defined in the first opposed surface 22, and a fluid slot 28 defined in the second opposed surface 24.

As shown in FIG. 2A, the die 12 may include two portions 12', 12", one (12') of which forms the first opposed surface 22 and the other (12") of which forms the second opposed surface. In an embodiment, the portion 12" of the die 12 is fabricated from a glass or silicon-based material, and/or any other suitable material capable of being immersed into a fluid without undesirable levels of corrosion, swelling, fracture/cracking, delamination, and/or disfigurement resulting therefrom. The portion 12' of the die 12 is formed of a polymer, which attaches to the portion 12".

The die 12 may be formed (e.g., via sawing, scribing, cleaving, and/or micro-machining techniques) into any desired configuration (i.e., size and/or shape) that enables the die 12 to be loaded with fluid via contact with a fluid, or via partial or complete immersion into a fluid source, e.g., a well-plate. Other suitable methods for loading the die 12 include using a pipette, syringe, pin, or puddle to contact the die 12 with fluid at an appropriate loading location.

While any suitable fluid source may be used, non-limiting examples of fluid source well-plates include 96 well-plates having a well diameter of about 6 mm, 384 well-plates having a well diameter of about 4 mm, 1536 well-plates having an inner well diameter of about 2 mm I.D., or combinations thereof. In an embodiment, the portion 12" of the die 12 has a three-dimensional rectangular geometric configuration that has a length L ranging from about 0.5 mm to about 4 mm, a width (not shown) ranging from about 0.3 mm to about 4 mm, and a height H ranging from about 0.3 mm to about 2 mm. The other portion 12' of the die 12 has a thickness ranging from about 10 μm to about 60 μm. It is to be understood that the die 12 may be configured to be larger or smaller, depending, at least in part on the fluid source location used with the fluid transfer device 10.

As previously stated, FIGS. 1B and 2A illustrate the die 12, which includes first and second opposed surfaces 22, 24, where at least one nozzle 26 is formed or otherwise defined in the first opposed surface 22, and a fluid slot 28 is formed or otherwise defined in the second opposed surface 24. In a non-limiting example, the nozzle(s) 26 and the fluid slot 28 are formed in the die 12 via, for example, micro-machining or other suitable thin-film deposition techniques.

While two nozzles 26 are shown in FIG. 2A, it is to be understood that any number of nozzles 26 may be formed in the die 12. In an embodiment, the number of nozzles 26 formed in the die 12 ranges from about 2 to about 100. As a non-limiting example, each nozzle 26 may have a diameter ranging from about 5 μm to about 100 μm.

In an embodiment, the fluid slot 28 includes an inlet 30 defined in the second opposed surface 24, and an outlet 32 located or positioned at an end of the fluid slot 28 generally opposed to the inlet 30, such that the outlet 32 is in fluid communication with the nozzle(s) 26 (formed in the first opposed surface 22). As shown in FIG. 2A, the fluid slot 28 may include more than one outlet 32. It is to be understood that each outlet 32 is in fluid communication with at least one nozzle 26.

Figure 2B:
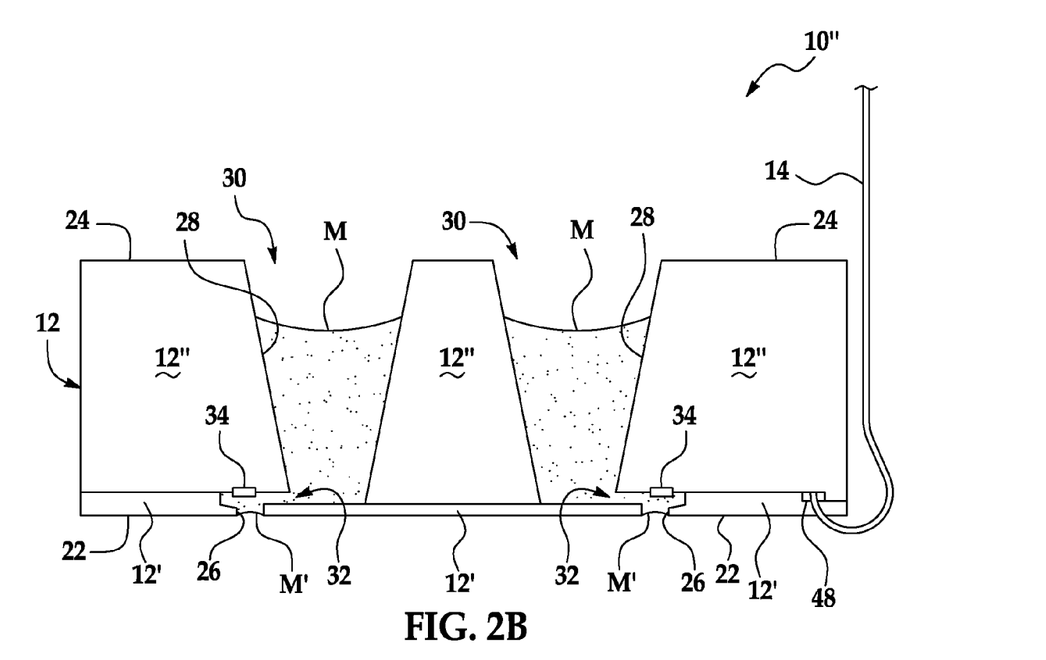
FIG. 2B is a cross-sectional cut-away view of an embodiment of the fluid transfer device including two fluidly separate slots.
Figure 4:
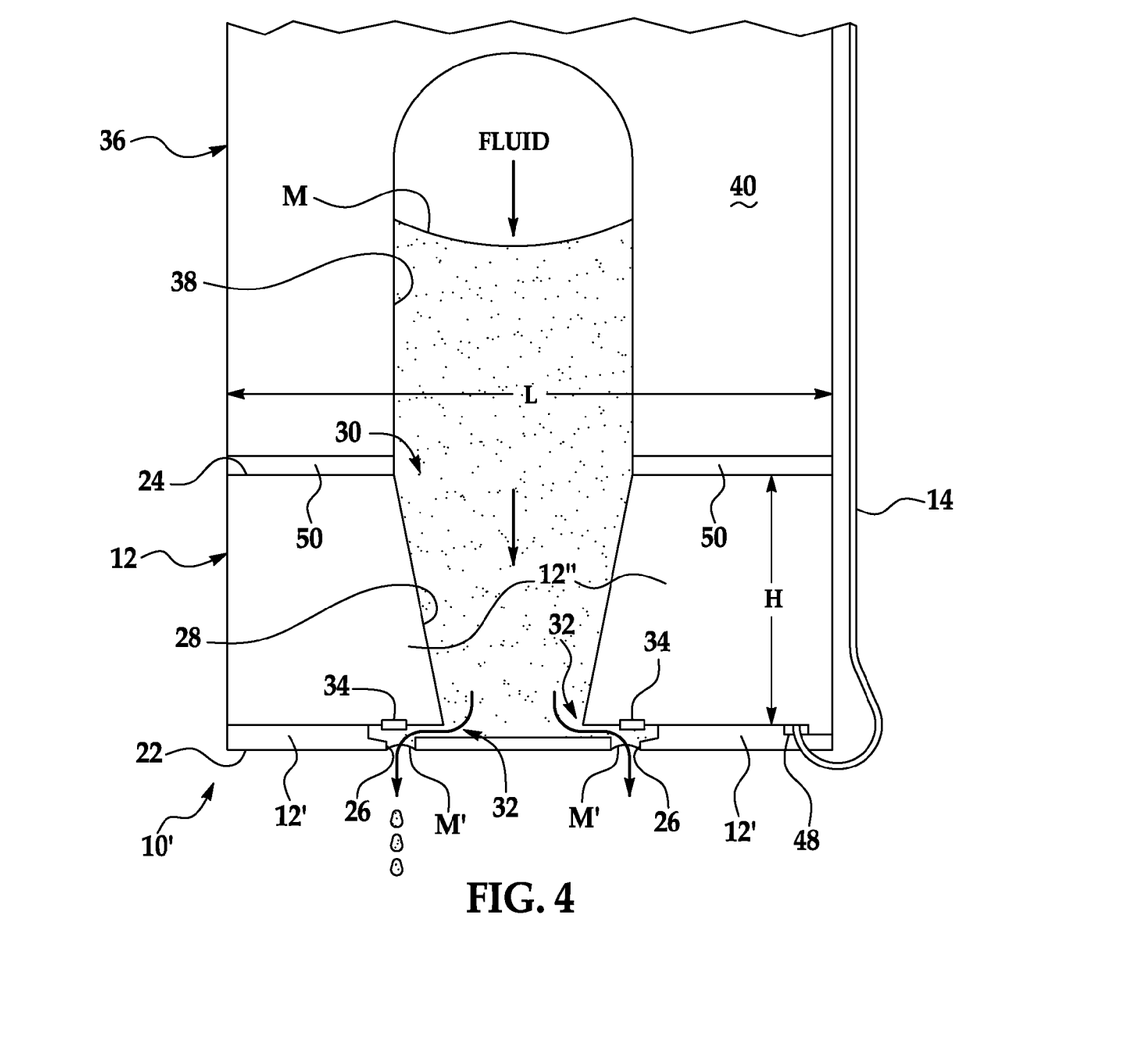
FIG. 4 is a cross-sectional cut-away view of the embodiment of the fluid transfer device taken along line 4-4 of FIG. 3, wherein the device is filled with a sample fluid and the black lines indicated sample fluid flow upon ejection.

The fluid slot 28 is generally tapered such that an inlet 30 width is larger than a width of the opposed end of the fluid slot 28 (as shown in FIGS. 2A, 2B and 4). Generally, the various widths of the fluid slot 28 range from about 100 μm to about 600 μm.

The nozzles 26 and the inlet 30 enable a fluid sample to wick into the fluid slot 28 when the die 12 is at least partially contacted with or at least partially immersed in the fluid sample. The outlet 32 enables the fluid sample in the fluid slot 28 to transfer to the nozzle 26, from which the fluid sample is dispensed or otherwise ejected. It is to be understood that wicking of the fluid sample into the fluid slot 28 is accomplished via capillary action, i.e., due to adhesive and cohesive intermolecular forces, as well as surface tension, the fluid sample substantially spontaneously moves into the fluid slot 28 via the inlet 30 and via the nozzle(s) 26. It is to be further understood that wicking of the fluid sample is accomplished substantially without any external back-pressure.

In an embodiment, the fluid ejection device 10 is immersed into the fluid such that the nozzle(s) 26 make contact with the fluid first. In the event that the slot 28 is immersed before filling is complete, the fluid ejection device 10 will potentially fill from both the nozzle(s) 26 and the fluid slot 28. However, given the taper of the slot 28, it is believed that capillary forces will be stronger on the narrower portion, such that bubbles will naturally and more easily expel out of the inlet 30 of the slot 28.

The equation for capillary pressure is:

$$p_c = 2\gamma \cos \theta / r \qquad (1)$$

where γ is the surface tension of the fluid, θ is the contact angle of the fluid to the solid, and r is the capillary radius. Fluid filling tends to have more force in the smaller dimension features. As such, the nozzles 26 fill with fluid and air tends to be displaced out of the slot 28 via the inlet 30. It is believed that the differential filling rate of the nozzles 26 and inlet 30, and the ability to expel air substantially eliminates air trapping in the slot 28. To assure expelling of the bubbles, it may be advantageous to dip the fluid transfer device 10 at an orientation where the nozzles 26 make contact with the fluid prior to inlet 30 making contact with the fluid.

Equation 1 also illustrates that it is desirable that the contact angle be less than 90 degrees to achieve fluid filling. In some instances (e.g., when using aqueous solutions), this is achieved without additional treatment. In other instances, however, a desirable level of wetting may be achieved by adding surface active agents to the fluid, or by modifying the surface of the die 12 via plasma treatment or some other surface treatment.

Thus, a user of the fluid transfer device 10 disclosed herein is capable of filling the fluid slot 28 with a fluid sample by at least partially contacting or immersing the die 12 with or into the fluid source and allowing capillary action to draw the fluid in.

Both FIGS. 1B and 2A illustrate the fluid transfer device 10 having fluid wicked therein. The meniscus M adjacent the inlet 30 is shown in both figures, and the meniscus M' adjacent each nozzle 26 is shown in FIG. 2A.

Capillary action also maintains the fluid sample in the fluid slot 28 until the device 10 is actuated via a control device (described further hereinbelow). In an embodiment, the fluid slot 28 is capable of holding a fluid volume of less than 100 nL, or up to or greater than 10 μL. It is to be understood, however, that because fluid filling depends, at least in part, on capillary rise, the fill volume for a given geometry may have a limit. Greater volumes than this limit may be achieved, for example, by tilting the fluid slot 28 such that the capillary rise height is smaller, by extending the fluid slot 28 (see FIGS. 3 and 4), by including multiple smaller fluid slots 28 (see FIG. 2B), or by increasing the contact surface area and substantially filling the volume with foam or some other structure material (not shown). It is to be further understood that while the fluid slot 28 may hold a predetermined fluid volume, any desirable fluid volume that is equal to or less than the predetermined fluid volume may be dispensed from the device 10. In a non-limiting example, the fluid slot 28 may hold about 1 μL of fluid, and droplets of, for example, about 1 nL and/or 1 pL may be controllably dispensed. In one embodiment, to dispense a desired volume, the fluid slot 28 is loaded with a greater volume than the desired volume (up to the loading limit), which allows for the possibility that some minute volume may be stranded in the device 10. It is to be understood that many droplets may also be dispensed to deliver the sum of their volumes, as desired.

The control device generally includes a fluid ejection device 34 operatively connected to the drive mechanism via an electrical interconnect 14. The volume of fluid dispensed into or onto the fluid destination (not shown) is generally controlled by the fluid ejector 34 in response to electrical commands from the drive mechanism.

FIG. 2A illustrates two fluid ejection devices 34 integrated in the die 12. In an embodiment, each fluid ejection device 34 is in fluid communication with one outlet 32 of the fluid slot 28 and with one nozzle 26. As shown in FIG. 2A, the respective fluid ejection devices 34 are positioned opposite the respective nozzles 26, in order to facilitate ejection of the fluid sample from the respective nozzle(s) 26. In a non-limiting example, the die 12 includes a single fluid slot 28, a plurality of nozzles 26 and respective associated fluid ejection devices 34 in fluid communication with the single fluid slot 28.

In an embodiment, the fluid ejection device(s) 34 are inkjet dispensers. The fluid ejection device(s) 34 may be drop-on-demand (DOD) dispensers, such as thermal inkjet dispensers (i.e., thin-film resistors) or piezo-electric inkjet dispensers (i.e., piezo-electric films).

As previously stated, the fluid ejection devices 34 are operatively connected to the electrical interconnect member 14, which is ultimately electrically connected to a drive mechanism. As shown in FIG. 1A, a plurality of electrical pins 16 may connect the interconnect member 14 to the drive mechanism (not shown). The drive mechanism controls the electronics throughout the system 20 and actuates one or more of the fluid ejection devices 34 sequentially and/or simultaneously. The interconnect member 14 may be electrically connected to bond pads 48, which are operatively integrated in the portion 12' of the die. The fluid ejection device(s) 34 are also electrically connected to the bond pads 48 via conductive traces extending between die portions 12', 12". It is to be understood that the drive mechanism may be permanently attached or removably attached to the fluid transfer device 10.

Another embodiment of the fluid transfer device 10" is shown in FIG. 2B. In this embodiment, a plurality of fluid slots 28 is formed in the die 12. Each fluid slot 28 has a respective inlet 30 and outlet 32, and is associated with respective nozzle(s) 26 and ejection device(s) 34. As shown, the slots 28 (and components associated therewith) are fluidly separated, which enables separate loading and separate dispensing.

Figure 3:
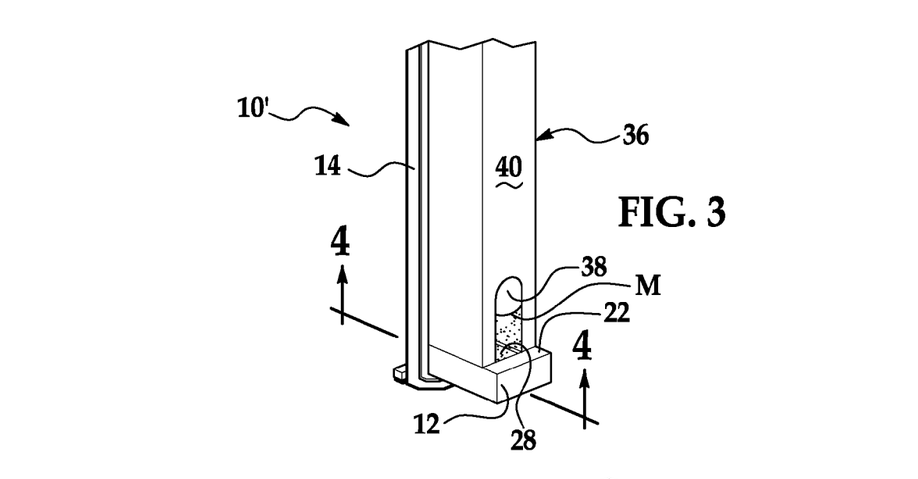
FIG. 3 is a perspective cut-away view of another embodiment of the fluid transfer device.

Still another embodiment of the fluid transfer device 10' is shown in FIGS. 3 and 4. In this embodiment, the volume of the fluid slot 28 is expanded by operatively connecting a member 36 to the die 12. The member 36 includes a body portion 40 that defines a fluid slot 38 and is attached to the die 12. Any suitable attachment mechanism may be employed, including adhesive 50 shown in FIG. 4. In an embodiment, the length of the body 40 is positioned proximate to a portion of the interconnect member 14. It is to be understood that the member 36 may be formed from any suitable material, a non-limiting example of which is a molded polymeric material, such as polycarbonate, polystyrene, polypropylene, poly-olefins, acrylates, or combinations thereof.

The body 40 of the member 36 defines the fluid slot 38. The member fluid slot 38 may be configured to expand the fluid slot 28 volume up to several μL. In a non-limiting example, the member fluid slot 38 expands the fluid slot 28 volume anywhere from about 100 nL to about 10 μL. Generally, the member 36 may be placed on the first opposed surface 22 of the die 12, such that at least a portion of the member fluid slot 38 is substantially aligned with the die fluid slot 28. In one embodiment, the member fluid slot 38 is directly aligned with the fluid slot 28.

It is to be understood that the member fluid slot 38 may also be configured to have other geometries. In one non-limiting example (not shown), the member fluid slot 38 substantially aligns with the die fluid slot 28 at an area directly adjacent the die fluid slot 28, and then the member fluid slot 38 branches or splits into multiple fluidic arms, each of which receives the sample fluid. These fluidic arms are believed to increase capillary volume by increasing contact surface area and decreasing capillary rise. In another non-limiting example (also not shown), the member fluid slot 38 has a length that extends beyond the length L of the die fluid slot 28, thereby increasing capillary volume.

The member fluid slot 38 performs substantially the same function as the fluid slot 28, i.e., to wick fluid from a fluid source to which it is at least partially exposed. The wicking of the fluid into the member fluid slot 38, in combination with the wicking of the fluid into the die fluid slot 28 enables the fluid transfer device 10' to obtain and hold a substantially higher volume of fluid (than the fluid slot 28 alone). Since the two slots 28, 38 may store more fluid than the fluid slot 28 alone, it is to be understood that larger volumes of fluid may be dispensed, if desired. In a non-limiting example, the combination of the fluid slots 28, 38 may enable wicking of several microliters (μL) into the slots 28, 38, and as such, volumes ranging from as small as approximately 1 pL up to the entire volume of the slots 28, 38 may be dispensed.

Both FIGS. 3 and 4 illustrate the fluid transfer device 10' having fluid wicked therein. The meniscus M in the member fluid slot 38 is shown in both figures, and the meniscus M' adjacent each nozzle 26 is shown in FIG. 4.

It is to be understood that the embodiment of the fluidic transfer device 10" shown in FIG. 2B may also include the member fluid slot 38. In this embodiment, each of the plurality of fluid slots 28 may have a member fluid slot 38 associated therewith. The member fluid slots 38 may be configured similar to the embodiment shown in FIGS. 3 and 4, such that each of the member fluid slots 38 substantially vertically extends a respective one of the die fluid slots 28 (i.e., interior walls of the member fluid slots 38 are substantially perpendicular to the die second opposed surface 24). In another embodiment, the member fluid slots 38 substantially align with the die fluid slots 28, but the interior walls of each member fluid slot 38 are angled with respect to the die second opposed surface 24.

Upon dispensing fluid from the nozzles 26, the depleted fluid volume will be compensated by movement of the slot meniscus M towards the nozzle meniscus M'. At the location of the nozzle 26, the meniscus M' is pinned by high capillary pressure, and conversely, the slot meniscus M is relatively moveable due, at least in part, to the larger dimensions, modest taper, and accordingly lower capillary pressure.

Figure 5:
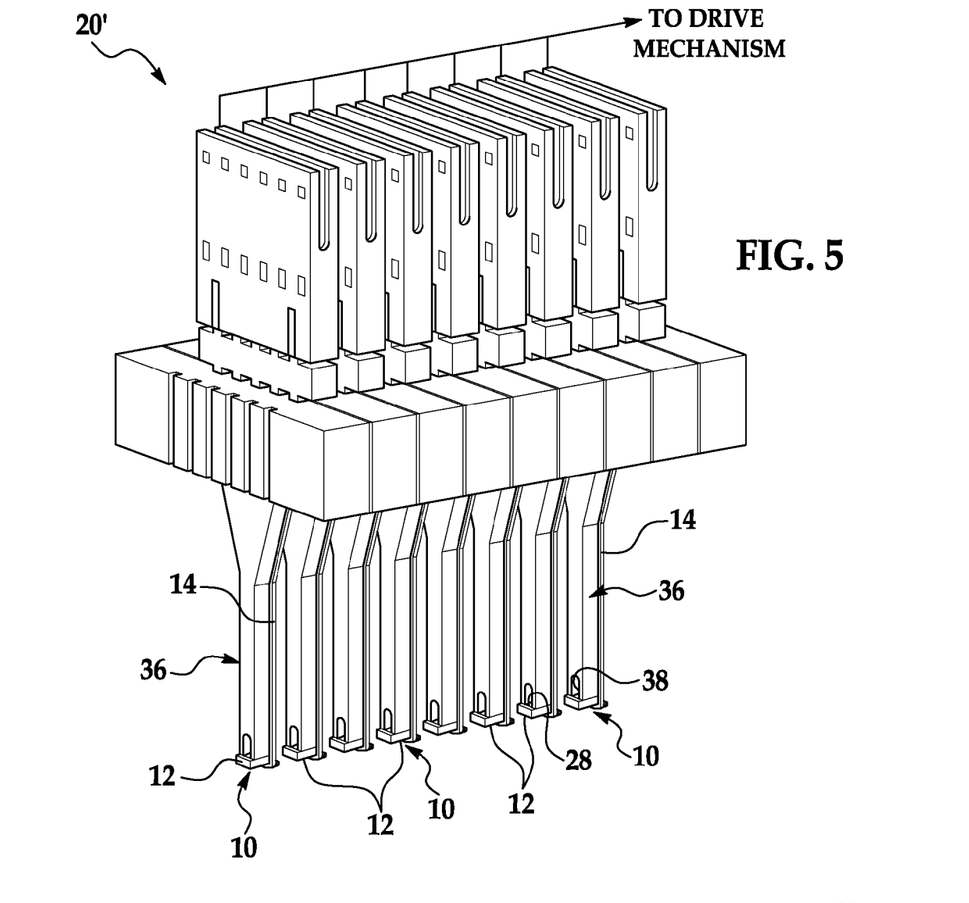
FIG. 5 is a perspective, semi-schematic view of an embodiment of a fluid transfer system including a plurality of fluid transfer devices operatively connected to a drive mechanism, each of the devices including a member with a second fluid slot.

Yet another embodiment of the fluid transfer system 20' is semi-schematically shown in FIG. 5. This embodiment of the fluid transfer system 20 includes a plurality of individual fluid transfer devices 10' each of which is connected to the drive mechanism. As previously mentioned, the drive mechanism operatively controls the fluid ejection device(s) 34 of each fluid transfer device 10, 10', 10" such that a predetermined volume of the fluid sample for each individual fluid transfer device 10, 10', 10" may be dispensed into or onto one or more fluid destinations.

In this embodiment, the transfer of one or more fluid samples during a single delivery may be controlled. As such, any number of the fluid transfer devices 10, 10', 10" in the system 20' may be used. It is to be understood that each fluid transfer device 10, 10', 10" may also be individually electrically addressed (via the control electronics, i.e., drive mechanism, interconnect 14, fluid ejector device 34, etc.) to dispense substantially the same volume of fluid or different volumes of fluid into/onto the same or different fluid destinations. It is to be further understood that each fluid transfer device 10, 10', 10" may be configured to wick and hold substantially the same volume, or different volumes.

Figure 6:
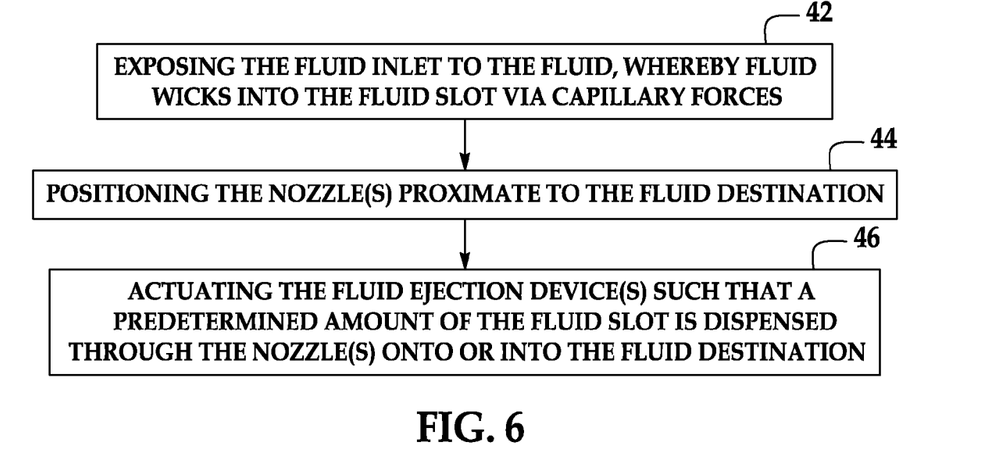
FIG. 6 is a flow diagram of an embodiment of a method of transferring a fluid using the fluid transfer device of FIG. 1A.

A method of transferring the fluid using embodiments of the device 10, 10', 10" and/or system 20, 20' is depicted in FIG. 6. The method includes exposing the fluid inlet 30 to the fluid, whereby fluid wicks into the fluid slot 28 via capillary forces (Block 42); positioning the nozzle(s) 26 proximate to the fluid destination (Block 44); and actuating the fluid ejection device(s) 34 such that a predetermined amount of the fluid in the fluid slot 28 is dispensed through the nozzle(s) 26 onto or into the fluid destination (Block 46). In this method, actuating the fluid ejection device(s) 34 includes activating at least one of the nozzle(s) 26 via the control electronics.

In an embodiment, after the fluid wicks into the fluid slot 28 (Block 42), the method may further include clearing drop ejection of the fluid ejection devices 34 into a waste receptacle, such as, for example, a specific well of a well-plate designated for waste drop collection. It is to be understood that such clearing drop ejections may be accomplished multiple times before actual transfer of the fluid sample. It is to be further understood that clearing drop ejection may be performed with or without ejecting fluid by setting the firing energy to a suitable level. This may be accomplished, at least in part, to achieve substantially steady state drop ejection of the ejection device(s) 34.

The control electronics may be programmed to automatically dispense a predetermined volume of fluid onto or into a predetermined destination. Non-limiting examples of suitable fluid destinations include a substantially flat substrate, nitro-cellulose membranes, a well of a well-plate or specific locations therein, an electrostatic cavity, a quartz crystal resonator, a cantilever for a micro-electromechanical system, and/or the like, and/or combinations thereof. It is to be understood that a user may input data to program the control electronics. Each system 20, 20' may, for example, be a handheld system whose movement is controlled by a user, an automated system whose movement is controlled by an automated x, y, z stage, or a combination of a handheld and an automated system.

In a non-limiting example, the method disclosed herein may be used to transfer fluids to a substantially flat substrate to produce test strips. In a further non-limiting example, the fluid transfer method includes controlling actuation of the fluid ejection device(s) 34 and controlling the relative speed of a single fluid transfer device 10, 10', 10" with an automated x, y, z stage during drop ejection to produce test strips with gradients of drop density on the substantially flat substrate. For example, by ejecting one drop from one nozzle, a fluid volume ranging from about 1 pL to about 100 pL may be dispensed, and by ejecting 1000 drops from 10 nozzles, a fluid volume ranging from about 10 nl to about 1 μL may be dispensed. As such, a range of 1 pL to 1 μL (six orders of magnitude) of a fluid may be directly jetted from the fluid transfer device 10, 10', 10" onto a single substrate.

The fluid transfer device 10, 10', 10" disclosed herein is also configured for substantially simplified cleaning method(s), which may be performed before and/or after use thereof. The cleaning method(s) may be incorporated with the method of transferring the sample fluid into or onto the fluid destination, which substantially simplifies sample fluid handling or transfer cycles. It is to be understood, however, that the cleaning method(s) may also be used separately from the method of transferring the sample fluid into or onto the fluid destination.

An embodiment of the cleaning method includes exposing the fluid inlet 30 to a cleaning solution, whereby the cleaning solution wicks into the fluid slot 28 via capillary forces. In a non-limiting example, exposure of the fluid inlet 30 to the cleaning solution is accomplished, for example, by submerging the die 12 in the cleaning solution.

A non-limiting example of a suitable cleaning solution is a surfactant solution, where the surfactant is selected from sodium dodecyl sulfate. Other suitable surfactants include anionic and nonionic surfactants. Examples of anionic surfactants include, but are not limited to sulfonate surfactants such as sulfosuccinates (Aerosol OT, A196; AY and GP, available from CYTEC) and sulfonates (Aerosol DPOS45, OS available from CYTEC; Witconate C-50H available from WITCO; Dowfax 8390 available from DOW); and fluoro surfactants (Fluorad FC99C available from 3M). Examples of nonionic surfactants include, but are not limited to fluoro surfactants (Fluorad FC170C available from 3M); alkoxylate surfactants (Tergitol series 15S-5, 15S-7, and 15S-9 available from Union Carbide); and organosilicone surfactants (Silwet L-77 and L-76-9 available from WITCO). Cationic surfactants, including cetyltrimethylammonium bromide (Aldrich)

may be undesirable in some embodiments as they tend to precipitate anionic materials, such as proteins. It is to be understood that cationic surfactants may be desirable in some other embodiments.

The cleaning solution may also include buffers to control pH; metal chelators to solubilize metal precipitates, such as calcium carbonate; and biocides to inhibit microbial growth. Such ingredients are further described in U.S. Pat. No. 6,610,129, issued Aug. 26, 2003, incorporated herein by reference in its entirety.

In this embodiment, the cleaning method further includes actuating the fluid ejection device(s) 34 such that the cleaning solution is dispensed through the nozzle(s) 26. The fluid ejection device(s) 34 may be actuated multiple times (e.g., about a hundred times at an actuation frequency of about 1 kHz) to dispense the cleaning solution from the device 10, 10', 10", may be actuated at substantially low levels of energy (i.e., an energy level sufficient to produce vapor bubble nucleation without producing a single strong drive bubble), and/or combinations thereof. In a non-limiting example, the die 12 is first removed from the cleaning solution, and then the ejection devices (34) are actuated, thereby dispensing the cleaning fluid. In another non-limiting example, actuation of the ejection device(s) 34 is accomplished while the die 12 is submerged in the cleaning solution.

Another embodiment of the cleaning method includes immersing the die 12 in the cleaning solution, rinsing the die 12 with water, and drying the die 12. Still another embodiment of the cleaning method includes exposing the die 12 to a jet stream of the cleaning solution.

It is to be understood that since the interconnect member 14 is positioned in close proximity to the die 12, the interconnect member 14 may potentially be susceptible to contamination from exposure to, for example, other fluids, bacteria, and/or the like. Such contamination often results from prolonged or residual exposure of the interconnect member 14 to water or other fluids. Thus, to substantially reduce the risk of, or prevent such contamination, at least a portion of the interconnect member 14 located directly adjacent to the die 12 may be treated to render the portion of the member 14 hydrophobic. This hydrophobic coating is believed to substantially prevent fluid (e.g., water) from wetting of the member 14 when immersed in the fluid. Examples of such treatment coatings include photoimagable epoxies, such as SU8, or other hydrophobic polymers, such as fluoropolymers. In one embodiment, the member 14 is rendered hydrophobic using a mask and vapor deposition.

While several embodiments have been described in detail, it will be apparent to those skilled in the art that the disclosed embodiments may be modified and/or other embodiments may be possible. Therefore, the foregoing description is to be considered exemplary rather than limiting.

What is claimed is:

1. A fluid delivery system, comprising:
a drive mechanism; and
a fluid transfer device operatively connected to the drive mechanism, the fluid transfer device including:
one die having first and second opposed surfaces;
at least one nozzle formed in the first opposed surface;
one fluid slot formed in the second opposed surface, the one fluid slot having an inlet adjacent the second opposed surface, and a separate outlet through which fluid exits to the at least one nozzle, the one fluid slot to wick fluid into the fluid slot and to contain the fluid in the die via capillarity and substantially without any external back pressure; and
a fluid ejection device in fluid communication with the fluid slot and the at least one nozzle, the fluid ejection device being operatively connected to the drive mechanism;
the first opposed surface being a continuous surface except where the at least one nozzle is formed.

2. The fluid delivery system as defined in claim 1, further comprising a plurality of fluid transfer devices, each of which is individually and operatively connected to the drive mechanism.

3. The fluid delivery system as defined in claim 1, further comprising an electrical interconnect member operatively connecting the one die to the drive mechanism.

4. The fluid delivery system as defined in claim 3 wherein at least a portion of the electrical interconnect member directly adjacent to the one die is treated to render the at least a portion of the electrical interconnect member hydrophobic.

5. The fluid delivery system as defined in claim 1, further comprising a member having a second fluid slot defined therein, the member being operatively connected to the one die such that at least a portion of the second fluid slot is substantially aligned with at least a portion of the fluid slot.

6. The fluid delivery system as defined in claim 1 wherein the inlet and the second opposed surface are open to an external atmosphere.

7. A method of making a fluid delivery system, comprising:
defining a fluid slot in a die such that a fluid inlet of the fluid slot is adjacent one of two opposed surfaces of the die;
defining at least one nozzle in an other of the two opposed surfaces of the die, the other of the two opposed surfaces being a continuous surface except where the at least one nozzle is formed, whereby the at least one nozzle is fluidly connected to an outlet of the fluid slot;
configuring a fluid ejection device in the die such that the fluid ejection device is capable of ejecting fluid through the at least one nozzle; and
operatively connecting the fluid ejection device to a drive mechanism;
wherein the fluid slot is configured such that capillary forces substantially without external back pressure i) wick fluid through the fluid inlet into the fluid slot when the fluid slot is exposed to the fluid, and ii) contain the fluid in the die.

8. The method as defined in claim 7, further comprising operatively connecting a member having a second fluid slot defined therein to the die such that the second fluid slot is substantially aligned with the fluid slot, thereby expanding a volume of the fluid slot.

9. The method as defined in claim 7 wherein defining the fluid slot in the die includes defining one fluid slot in one die.

10. A fluid delivery system, comprising:
a drive mechanism; and
a fluid transfer device operatively connected to the drive mechanism, the fluid transfer device including:
one die having first and second opposed surfaces;
at least one nozzle formed in the first opposed surface;
one fluid slot formed in the second opposed surface, the one fluid slot having an inlet adjacent the second opposed surface through which fluid wicks into the fluid slot via capillarity, and a separate outlet through which fluid exits to the at least one nozzle; and
a fluid ejection device in fluid communication with the fluid slot and the at least one nozzle, the fluid ejection device being operatively connected to the drive mechanism;
the first opposed surface being a continuous surface except where the at least one nozzle is formed;

wherein the one die includes two portions, wherein the first portion of the one die has a three-dimensional rectangular geometric configuration that has a length ranging from about 0.5 mm to about 4 mm, a width ranging from about 0.3 mm to about 4 mm, and a height ranging from about 0.3 mm to about 2 mm, wherein the second portion has a thickness ranging from about 10 μm to about 60 μm, and wherein the first opposed surface is defined on the second portion of the one die and the second opposed surface is defined on the first portion of the one die, the first portion being directly attached to the second portion.

11. A fluid delivery system, comprising:
a drive mechanism; and
a fluid transfer device operatively connected to the drive mechanism, the fluid transfer device including:
one die having first and second opposed surfaces;
at least one nozzle formed in the first opposed surface;
one fluid slot formed in the second opposed surface, the one fluid slot having an inlet adjacent the second opposed surface through which fluid wicks into the fluid slot via capillarity, and a separate outlet through which fluid exits to the at least one nozzle; and
a fluid ejection device in fluid communication with the fluid slot and the at least one nozzle, the fluid ejection device being operatively connected to the drive mechanism;
the first opposed surface being a continuous surface except where the at least one nozzle is formed, and the inlet and the second opposed surface being open to an external atmosphere.

12. The fluid delivery system as defined in claim 11 wherein the one die includes two portions, wherein the first portion of the one die has a three-dimensional rectangular geometric configuration that has a length ranging from about 0.5 mm to about 4 mm, a width ranging from about 0.3 mm to about 4 mm, and a height ranging from about 0.3 mm to about 2 mm, wherein the second portion has a thickness ranging from about 10 μm to about 60 μm, and wherein the first opposed surface is defined on the second portion of the one die and the second opposed surface is defined on the first portion of the one die, the first portion being directly attached to the second portion.

* * * * *